United States Patent
Zhou et al.

(10) Patent No.: US 10,496,748 B2
(45) Date of Patent: Dec. 3, 2019

(54) METHOD AND APPARATUS FOR OUTPUTTING INFORMATION

(71) Applicant: Baidu Online Network Technology (Beijing) Co., Ltd., Beijing (CN)

(72) Inventors: Jingbo Zhou, Beijing (CN); Yuan Xia, Beijing (CN); Hongliang Fei, Beijing (CN); Chaochun Liu, Beijing (CN); Weishan Dong, Beijing (CN); Wei Fan, Beijing (CN)

(73) Assignee: Baidu Online Network Technology (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/134,641

(22) Filed: Sep. 18, 2018

(65) Prior Publication Data
US 2019/0114318 A1  Apr. 18, 2019

(51) Int. Cl.
| | | |
|---|---|---|
| G06F 17/27 | (2006.01) | |
| G16H 50/00 | (2018.01) | |
| G06N 20/00 | (2019.01) | |
| G06F 16/31 | (2019.01) | |
| G06F 16/35 | (2019.01) | |
| G06F 16/903 | (2019.01) | |
| G06F 17/21 | (2006.01) | |

(52) U.S. Cl.
CPC ......... *G06F 17/278* (2013.01); *G06F 16/313* (2019.01); *G06F 16/355* (2019.01); *G06F 16/90335* (2019.01); *G06F 17/277* (2013.01); *G06N 20/00* (2019.01); *G16H 50/00* (2018.01)

(58) Field of Classification Search
CPC ............ G06F 17/278; G06F 16/90335; G06F 17/277; G06F 16/355; G06F 16/313; G06F 20/00; G16H 50/00
USPC ......................................................... 704/9
See application file for complete search history.

*Primary Examiner* — Thierry L Pham
(74) *Attorney, Agent, or Firm* — Miller, Matthias & Hull LLP (57) ABSTRACT

A method and apparatus for outputting information are provided. A specific embodiment of the method comprises: retrieving at least one medical entity keyword and at least one attribute keyword from a target medical text; then generating a set of keyword pairs, each of the keyword pairs including the retrieved medical entity keyword and the retrieved attribute keyword; then retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs; and finally outputting the keyword pairs having the association relationship in the set of keyword pairs. The embodiment improves the abundance of outputted information contents.

19 Claims, 5 Drawing Sheets

METHOD AND APPARATUS FOR OUTPUTTING INFORMATION

CROSS-REFERENCE TO RELATED APPLICATIONS

This application claims priority to Chinese Patent Application no. 201710972236.5, filed with the China National Intellectual Property Administration (CNIPA) on Oct. 18, 2017, the contents of which are incorporated herein by reference in their entirety.

TECHNICAL FIELD

Embodiments of the disclosure relate to the field of computer technology, specifically to the field of medical entity keyword recognition technology, and more specifically to a method and apparatus for outputting information.

BACKGROUND

An important area of electronic medical document analysis is retrieving a medical entity keyword. The medical entity keyword here includes keywords in the medical text, such as a disease, a symptom, a drug, and a body part. The retrieval of medical entity keywords has been widely used in structuring electronic documents, including disease statistics, symptom collection, and drug effect analysis.

SUMMARY

An object of some embodiments of the disclosure is to present a method and apparatus for outputting information.

In a first aspect, an embodiment of the disclosure provides a method for outputting information. The method includes: retrieving at least one medical entity keyword and at least one attribute keyword from a target medical text; generating a set of keyword pairs, where a keyword pair includes the retrieved medical entity keyword and the retrieved attribute keyword; retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, where the association result is used for indicating whether an association relationship exists between two words in a word pair, and the association-relationship determination model is used for characterizing a corresponding relationship between the text characteristic and the association result; and outputting the keyword pairs having the association relationship in the set of keyword pairs.

In some embodiments, the method further includes establishing the association-relationship determination model. The establishing the association-relationship determination model includes: acquiring an initial association-relationship determination model and a predetermined set of sample data, where each of the sample data in the set of sample data includes a medical text, at least one sample word pair corresponding to the medical text, and a word-pair annotation result corresponding to the sample word pair, the sample word pair includes the medical entity keyword and the attribute keyword in the medical text, and the word-pair annotation result is used for indicating whether the association relationship exists between the medical entity keyword and the attribute keyword in the sample word pair; retrieving, for the each of the sample data in the set of sample data, and for each of the at least one sample word pair in the each of the sample data, the text characteristic of the each of the at least one sample word pair in the medical text of the each of the sample data; training the initial association-relationship determination model using a machine learning method with the text characteristic of the each of the at least one sample word pair in the each of the sample data in the set of sample data in the medical text of the each of the sample data as input data, and the word-pair annotation result corresponding to the each of the at least one sample word pair as corresponding output data; and determining the trained initial association-relationship determination model as the pre-trained association-relationship determination model.

In some embodiments, the association-relationship determination model includes at least one of following items: a gradient boosting decision tree, a support vector machine, or a neural network.

In some embodiments, the retrieving at least one medical entity keyword and at least one attribute keyword from a target medical text includes: tokenizing the target medical text to obtain a token sequence; and retrieving the at least one medical entity keyword from the token sequence based on a preset medical entity keyword dictionary.

In some embodiments, the retrieving at least one medical entity keyword and at least one attribute keyword from a target medical text includes: retrieving the at least one attribute keyword from the target medical text based on a preset regular expression.

In some embodiments, the retrieving at least one medical entity keyword and at least one attribute keyword from a target medical text includes: introducing the target medical text into a pre-trained medical entity keyword retrieval model to obtain the at least one medical entity keyword, where the medical entity keyword retrieval model is used for characterizing a corresponding relationship between the medical text and the medical entity keyword.

In some embodiments, the medical entity keyword retrieval model includes a long short-term memory network model, or a conditional random field model.

In some embodiments, the attribute keyword includes at least one of following items: an occurrence time keyword, an occurrence frequency keyword, a duration keyword, or an occurrence cause keyword.

In some embodiments, the outputting the keyword pairs having the association relationship in the set of keyword pairs includes: determining the medical entity keywords included in the keyword pairs having the association relationship in the set of keyword pairs; determining, for each of the determined medical entity keywords, the occurrence time keyword, the occurrence frequency keyword, the duration keyword, and the occurrence cause keyword of the each of the determined medical entity keywords in the keyword pairs having the association relationship in the set of keyword pairs; and outputting the each of the determined medical entity keywords, and the occurrence time keyword, the occurrence frequency keyword, the duration keyword, and the occurrence cause keyword of the each of the determined medical entity keywords in a preset format.

In a second aspect, an embodiment of the disclosure provides an apparatus for outputting information. The apparatus includes: a retrieval unit, configured for retrieving at least one medical entity keyword and at least one attribute keyword from a target medical text; a generation unit, configured for generating a set of keyword pairs, where a keyword pair includes the retrieved medical entity keyword and the retrieved attribute keyword; an association unit, configured for retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, where the association result is used for indicating whether an association relationship exists between two words in a word pair, and the association-relationship determination model is used for characterizing a corresponding relationship between the text characteristic and the association result; and an output unit, configured for outputting the keyword pairs having the association relationship in the set of keyword pairs.

In some embodiments, the apparatus further includes an association-relationship determination model establishing unit. The association-relationship determination model establishing unit includes: an acquisition module, configured for acquiring an initial association-relationship determination model and a predetermined set of sample data, where each of the sample data in the set of sample data includes a medical text, at least one sample word pair corresponding to the medical text and a word-pair annotation result corresponding to the sample word pair, the sample word pair includes the medical entity keyword and the attribute keyword in the medical text, and the word-pair annotation result is used for indicating whether the association relationship exists between the medical entity keyword and the attribute keyword in the sample word pair; a first retrieval module, configured for retrieving, for the each of the sample data in the set of sample data, and for each of the at least one sample word pair in the each of the sample data, the text characteristic of the each of the at least one sample word pair in the medical text of the each of the sample data; a training module, configured for training the initial association-relationship determination model using a machine learning method with the text characteristic of the each of the at least one sample word pair in the each of the sample data in the set of sample data in the medical text of the each of the sample data as input data, and the word-pair annotation result corresponding to the each of the at least one sample word pair as corresponding output data; and a first determination module, configured for determining the trained initial association-relationship determination model as the pre-trained association-relationship determination model.

In some embodiments, the association-relationship determination model includes at least one of following items: a gradient boosting decision tree, a support vector machine, or a neural network.

In some embodiments, the retrieval unit includes: a tokenizer module, configured for tokenizing the target medical text to obtain a token sequence; and a second retrieval module, configured for retrieving the at least one medical entity keyword from the token sequence based on a preset medical entity keyword dictionary.

In some embodiments, the retrieval unit includes: a third retrieval module, configured for retrieving the at least one attribute keyword from the target medical text based on a preset regular expression.

In some embodiments, the retrieval unit includes: an introduction module, configured for introducing the target medical text into a pre-trained medical entity keyword retrieval model to obtain the at least one medical entity keyword, where the medical entity keyword retrieval model is used for characterizing a corresponding relationship between the medical text and the medical entity keyword.

In some embodiments, the medical entity keyword retrieval model includes a long short-term memory network model, or a conditional random field model.

In some embodiments, the attribute keyword includes at least one of following items: an occurrence time keyword, an occurrence frequency keyword, a duration keyword, or an occurrence cause keyword.

In some embodiments, the output unit includes: a second determination module, configured for determining the medical entity keywords included in the keyword pairs having the association relationship in the set of keyword pairs; a third determination module, configured for determining, for each of the determined medical entity keywords, the occurrence time keyword, the occurrence frequency keyword, the duration keyword, and the occurrence cause keyword of the each of the determined medical entity keywords in the keyword pairs having the association relationship in the set of keyword pairs; and an output module, configured for outputting the each of the determined medical entity keywords, and the occurrence time keyword, the occurrence frequency keyword, the duration keyword, and the occurrence cause keyword of the each of the determined medical entity keywords in a preset format.

In a third aspect, an embodiment of the disclosure provides an electronic device, the electronic device including: one or more processors; and a memory for storing one or more programs, where the one or more programs enable, when executed by the one or more processors, the one or more processors to implement the method according to any one of the implementations in the first aspect.

In a fourth aspect, an embodiment of the disclosure provides a computer readable storage medium storing a computer program therein, where the computer program implements, when executed by a processor, the method according to any one of the implementations in the first aspect.

The method and apparatus for outputting information provided by the above embodiments of the disclosure retrieve at least one medical entity keyword and at least one attribute keyword from a target medical text; then generate a set of keyword pairs, where each of the keyword pairs includes the retrieved medical entity keyword and the retrieved attribute keyword; then retrieve, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, where the association result is used for indicating whether an association relationship exists between two words in a word pair, and the association-relationship determination model is used for characterizing a corresponding relationship between the text characteristic and the association result; and finally output the keyword pairs having the association relationship in the set of keyword pairs, thereby retrieving the attribute keyword having the association relationship with the medical entity keyword in the medical text, and improving the abundance of outputted information contents.

BRIEF DESCRIPTION OF THE DRAWINGS

By reading and referring to detailed description on the non-limiting embodiments in the following accompanying drawings, other features, objects, and advantages of the disclosure will become more apparent.

DETAILED DESCRIPTION OF EMBODIMENTS

The present application will be further described below in detail in combination with the accompanying drawings and the embodiments. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that the embodiments in the present application and the features in the embodiments may be combined with each other on a non-conflict basis. The present application will be described below in detail with reference to the accompanying drawings and in combination with the embodiments.

Figure 1:
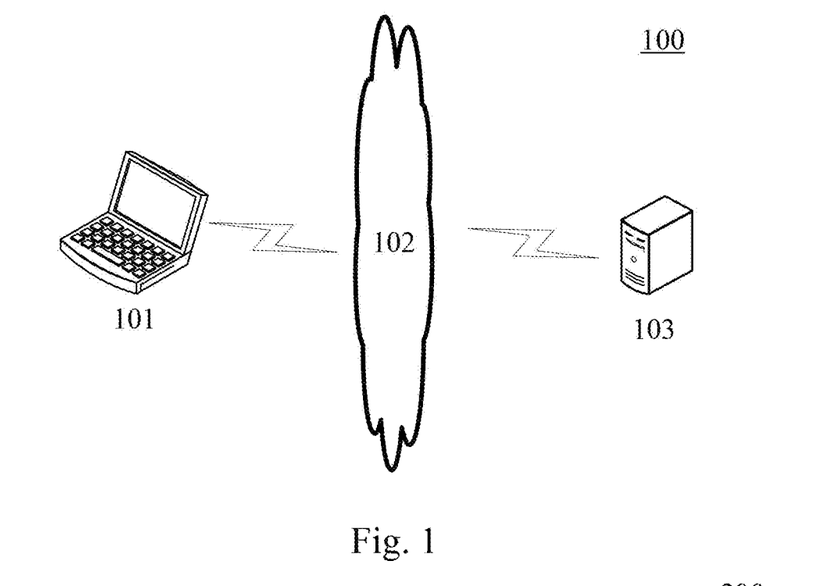
FIG. 1 is a structural diagram of an illustrative system in which the disclosure may be applied.

FIG. 1 shows an illustrative architecture of a system 100 which may be used by a method for outputting information or an apparatus for outputting information according to some embodiments of the present application.

As shown in FIG. 1, the system architecture 100 may include a terminal device 101, a network 102, and a server 103. The network 102 serves as a medium providing a communication link between the terminal device 101 and the server 103. The network 102 may include various types of connections, such as wired or wireless transmission links, or optical fibers.

The user may use the terminal device 101 to interact with the server 103 through the network 102, in order to transmit or receive messages, etc. Various communication client applications, such as text editor applications and webpage browser applications, maybe installed on the terminal device 101.

The terminal device 101 may be various electronic devices having a display and capable of editing text, including but not limited to, smart phones, tablet computers, laptop computers, and desktop computers.

The server 103 may be a server providing various services. The back-end server may perform corresponding processing, such as analysis, on various medical text data stored in the terminal device, and return a processing result (for example, the keyword pair including the one medical entity keyword and the attribute keyword and having the association relationship) to the terminal device.

It should be noted that the method for outputting information provided by an embodiment of the disclosure is generally executed by the server 103. Accordingly, the apparatus for outputting information is generally provided in the server 103. In some cases, the method for outputting information provided by an embodiment of the disclosure may also be executed by the terminal device 101. Accordingly, the apparatus for outputting information is generally provided in the terminal device 101. In this case, the system architecture 100 may include only the terminal 101 except the server 103. This is not limited in the disclosure.

It should be appreciated that the numbers of the terminal devices, the networks and the servers in FIG. 1 are merely illustrative. Any number of terminal devices, networks and servers may be provided based on the actual requirements.

Figure 2:
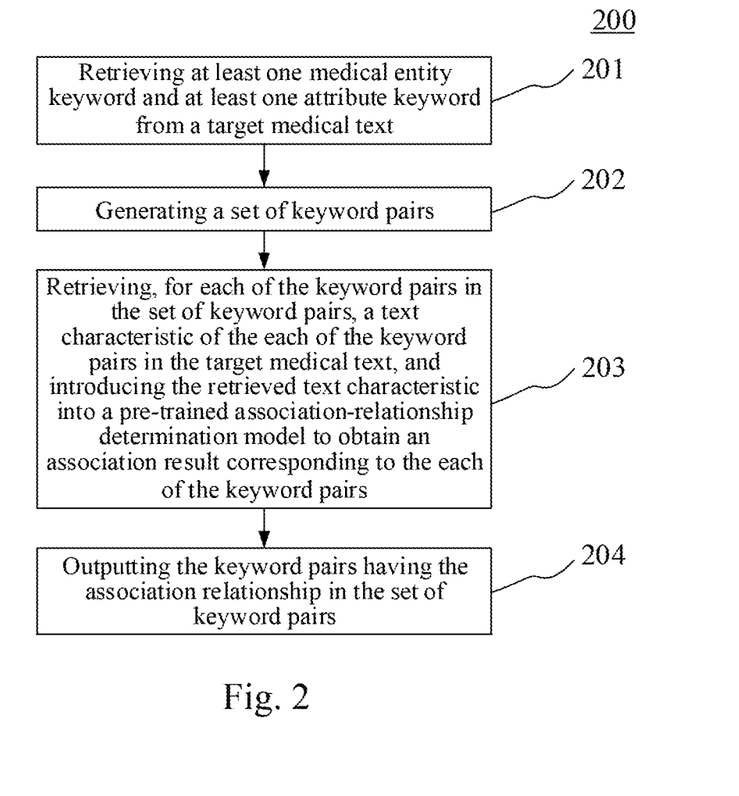
FIG. 2 is a process diagram of an embodiment of a method for outputting information according to the disclosure.

Further referring to FIG. 2, a process 200 of an embodiment of a method for outputting information according to the disclosure is shown. The embodiment is illustrated mainly by applying the method to an electronic device with a certain computing ability. The electronic device may be the server 103 shown in FIG. 1, or the terminal device 101 shown in FIG. 1. The method for outputting information includes:

Step 201: retrieving at least one medical entity keyword and at least one attribute keyword from a target medical text.

In the embodiment, an electronic device (e.g., the server shown in FIG. 1) on which the method for outputting information runs may retrieve at least one medical entity keyword and at least one attribute keyword from a target medical text.

In the embodiment, the target medical text may be either a medical-related text or a text file with medical-related file content. The medical-related text may include, but is not limited to, medical consultation patient data generated in an electronic information system of a hospital, online doctor-patient QA data generated on a medical website, a user's drug purchase inquiry record generated by online and offline pharmacies, and the like.

Here, the medical entity may include, but is not limited to, a disease, a symptom, a drug, and a body part in the medical text. The medical entity keyword may include, but is not limited to, a disease name, a symptom name, a drug name, a body part name. The attribute keyword is a keyword describing an attribute of the medical entity. For example, the disease occurrence time, occurrence frequency, occurrence cause, and the like may each be the attribute of the medical entity disease. As another example, for a medical text "recently chest pain frequently occurs, and lasts for about a few minutes each time," "chest pain" is a medical entity keyword, "recently" is an attribute keyword describing the attribute of the occurrence time of the medical entity "chest pain," "frequently occurs" is the attribute keyword describing the attribute of the occurrence frequency of the medical entity "chest pain," and "a few minutes" is the attribute keyword describing the attribute of the duration of the medical entity "chest pain".

In the embodiment, the electronic device may first retrieve at least one medical entity keyword from the target medical text, and then retrieve at least one attribute keyword from the target medical text; or the electronic device may first retrieve at least one attribute keyword from the target medical text, and then retrieve at least one medical entity keyword from the target medical text.

In some optional implementations of the embodiment, the retrieving at least one medical entity keyword from a target medical text may also include: first tokenizing the target medical text, to obtain a token sequence, and then retrieving the at least one medical entity keyword from the token sequence based on a preset medical entity keyword dictionary. The tokenizing a text is an existing technology widely researched and applied at present, and is not repeated any more here.

In some optional implementations of the embodiment, the retrieving at least one medical entity keyword from a target medical text may also include: introducing the target medical text into a pre-trained medical entity keyword retrieval model to obtain the at least one medical entity keyword, where the medical entity keyword retrieval model is used for characterizing a corresponding relationship between the medical text and the medical entity keyword. As an example, the medical entity keyword retrieval model may be a corresponding relationship list storing a plurality of corresponding relationships between the medical texts and the medical entity keywords, which is pre-established by technical personnel based on statistics of a considerable amount of medical texts and medical entity keywords.

In some optional implementations of the embodiment, the electronic device may pre-train the medical entity keyword retrieval model by:

first, acquiring an initial medical entity keyword retrieval model and a predetermined set of medical text sample data, where each of the medical text sample data includes a medical text and at least one medical entity keyword corresponding to the medical text;

then training the initial medical entity keyword retrieval model using a machine learning method with the medical text of the each of the medical text sample data in the set of medical text sample data as input data, and the at least one medical entity keyword in the each of the medical text sample data as corresponding output data; and finally, determining the trained initial medical entity keyword retrieval model as the pre-trained medical entity keyword retrieval model.

Optionally, the medical entity keyword retrieval model may include a long short-term memory (LSTM) network model, or a conditional random field (CRF) model.

In some optional implementations of the embodiment, the retrieving at least one attribute keyword from a target medical text may include: retrieving the at least one attribute keyword from the target medical text based on a preset regular expression. In practice, different regular expressions may be preset to retrieve different attribute keywords based on different attributes of the medical entity described by the attribute keywords. For example, the regular expression for retrieving the attribute keyword of the attribute of the occurrence time of the medical entity may be:

Regex_pattern=(.?)(year|month|week|day|hour) (since|beyond|after|occurrence)

In some optional implementations of the embodiment, the retrieving at least one attribute keyword from a target medical text may also include: pre-training an attribute keyword retrieval model in accordance with the method for retrieving at least one medical entity keyword from a target medical text based on machine learning according to the optional implementations, and then introducing the target medical text into the pre-trained attribute keyword retrieval model to obtain the at least one attribute keyword in the target medical text. The method for training an attribute keyword retrieval model may refer to relevant descriptions on training the medical entity keyword retrieval model, and thus is not repeated any more here.

Step 202: generating a set of keyword pairs.

In the embodiment, the electronic device may generate a set of keyword pairs after the retrieving at least one medical entity keyword and at least one attribute keyword from a target medical text. Each of the keyword pairs in the set of keyword pairs includes the medical entity keyword and the attribute keyword retrieved in the step 201.

Step 203: retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs.

In the embodiment, the electronic device may retrieve, for each of the keyword pairs in the set of keyword pairs generated in the step 202, a text characteristic of the each of the keyword pairs in the target medical text, and introduce the retrieved text characteristic into a pre-trained association-relationship determination model to obtain an association result corresponding to the each of the keyword pairs, where the association result is used for indicating whether an association relationship exists between two words in a word pair. That is, the association result corresponding to the each of the keyword pairs is used for characterizing whether there is a corresponding relationship between the medical entity keyword and the attribute keyword in the each of the keyword pairs. In practice, the value of the association result may be a value indicating that the association relationship exists or a value indicating that the association relationship does not exist. For example, "1" is a value indicating that the association relationship exists, while "0" is a value indicating that the association relationship does not exist.

It should be noted that the association-relationship determination model is used for characterizing a corresponding relationship between the text characteristic and the association result. As an example, the association-relationship determination model may be a corresponding relationship list storing a plurality of corresponding relationships between text characteristics and association results, which is pre-established by technical personnel based on statistics of a considerable amount of text characteristics and association results, or the association-relationship determination model may be a calculation formula for calculating one or more numerical values in the text characteristics to obtain the association results for characterizing, which is pre-established by technical personnel based on statistics of a considerable amount of data and is stored in the electronic device.

In the embodiment, the keyword pair includes the medical entity keyword and the attribute keyword retrieved from the target medical text in the step 201. Therefore, text characteristics of the medical entity keyword and the attribute keyword included in the keyword pair in the target medical text may be retrieved.

As an example, text characteristics of the medical entity keyword and the attribute keyword included in the keyword pair in the target medical text may include, but are not limited to, at least one of following items: a distance between a location of the medical entity keyword and a location of the attribute keyword in the target medical text, whether there is a duplicate character between the medical entity keyword and the attribute keyword, a dependency of the medical entity keyword and the attribute keyword in a parse tree corresponding to the keyword pair, or a distance between the medical entity keyword and the attribute keyword in the parse tree corresponding to the keyword pair, where the parse tree corresponding to the keyword pair is a parse tree obtained by analyzing sentences of the medical entity keyword and the attribute keyword in the keyword pair in the target medical text according to dependency grammar analysis.

In some optional implementations of the embodiment, the electronic device may pre-train the association-relationship determination model by:

first, acquiring an initial association-relationship determination model and a predetermined set of sample data. Each of the sample data in the set of sample data includes a medical text, at least one sample word pair corresponding to the medical text, and a word-pair annotation result corresponding to the sample word pair, the sample word pair includes the medical entity keyword and the attribute keyword in the medical text, and the word-pair annotation result is used for indicating whether the association relationship exists between the medical entity keyword and the attribute keyword in the sample word pair.

Then, retrieving, for the each of the sample data in the set of sample data, and for each of the at least one sample word pair in the each of the sample data, the text characteristic of the each of the at least one sample word pair in the medical text of the each of the sample data.

As will be appreciated, the text characteristic retrieved during the training the association-relationship determination model may be a text characteristic identical to the text characteristic of the each of the keyword pairs in the set of keyword pairs in the target medical text.

Then, training the initial association-relationship determination model using a machine learning method with the text characteristic of the each of the at least one sample word pair in the each of the sample data in the set of sample data in the medical text of the each of the sample data as input data, and the word-pair annotation result corresponding to the each of the at least one sample word pair as corresponding output data.

Finally, determining the trained initial association-relationship determination model as the pre-trained association-relationship determination model.

In some optional implementations of the embodiment, the association-relationship determination model may include at least one of following items: a gradient boosting decision tree (GBDT), a support vector machine (SVM), or a neural network (NN).

Step 204: outputting the keyword pairs having the association relationship in the set of keyword pairs.

In the embodiment, the electronic device may output the keyword pairs having the association relationship in the set of keyword pairs.

Here, the keyword pairs having the association relationship in the set of keyword pairs refer to each of the keyword pairs in the set of keyword pairs in the step 203. A text characteristic of the each of the keyword pairs is retrieved from the target medical text and introduced into a pre-trained association-relationship determination model to obtain the association result corresponding to the each of the keyword pairs. If the association result corresponding to the each of the keyword pairs is that the keyword pair has an association relationship, then the keyword pair is a keyword pair having the association relationship; and if the association result corresponding to the each of the keyword pairs is that the keyword pair does not have the association relationship, then the keyword pair is a keyword pair not having association relationship.

In some optional implementations of the embodiment, the keyword pairs having the association relationship in the set of keyword pairs may be presented in the electronic device (e.g., a display screen of the electronic device).

In some optional implementations of the embodiment, the electronic device may further send the keyword pairs having the association relationship in the set of keyword pairs to other electronic devices, to enable the other electronic devices to receive and display the keyword pairs having the association relationship in the set of keyword pairs.

Figure 3:
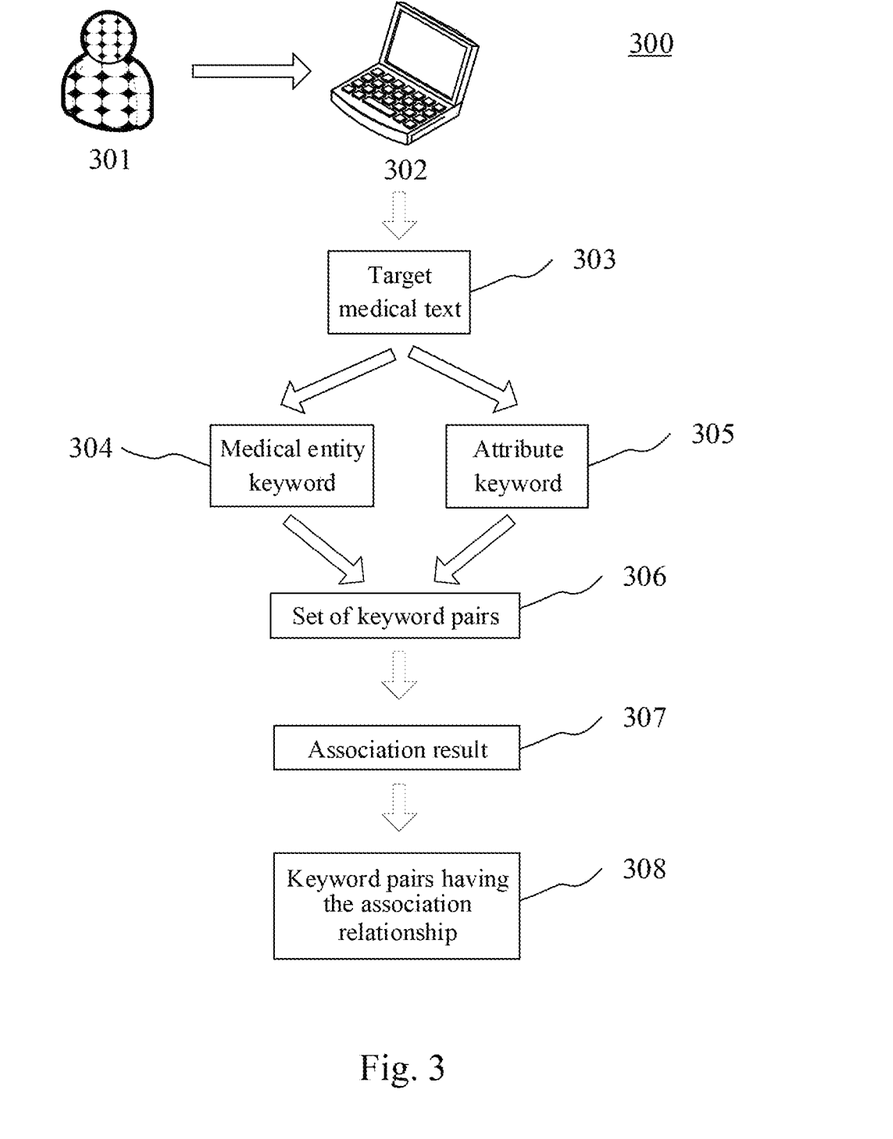
FIG. 3 is a schematic diagram of an application scenario of a method for outputting information according to the disclosure.

Further referring to FIG. 3, a schematic diagram of an application scenario of a method for outputting information according to the embodiment is shown. In the application scenario of FIG. 3, a user 301 first specifies a specified medical text in an electronic device 302 as a target medical text 303; then the electronic device 302 may retrieve a medical entity keyword 304 and an attribute keyword 305 from the target medical text 303; then the electronic device 302 may generate a set of keyword pairs 306 based on the medical entity keyword 304 and the attribute keyword 305; then the electronic device 302 may introduce a text characteristic of the each of the keyword pairs in the set of keyword pairs 306 in the target medical text 303 into a pre-trained association-relationship determination model to obtain an association result 307 of each of the keyword pairs in the set of keyword pairs; and finally, generating and outputting keyword pairs 308 having the association relationship in the set of keyword pairs 306 based on the association result 307.

The method provided by the above embodiments of the disclosure generates a set of keyword pairs based on at least one medical entity keyword and at least one attribute keyword retrieved from a target medical text; then introduces, for each of the keyword pairs in the set of keyword pairs, a text characteristic of the each of the keyword pairs in the target medical text into a pre-trained association-relationship determination model to obtain an association result corresponding to the each of the keyword pairs; and finally outputs the keyword pairs having the association relationship in the set of keyword pairs, thereby retrieving the attribute keyword having the association relationship with the medical entity keyword in the medical text, and improving the abundance of outputted information contents.

Figure 4:
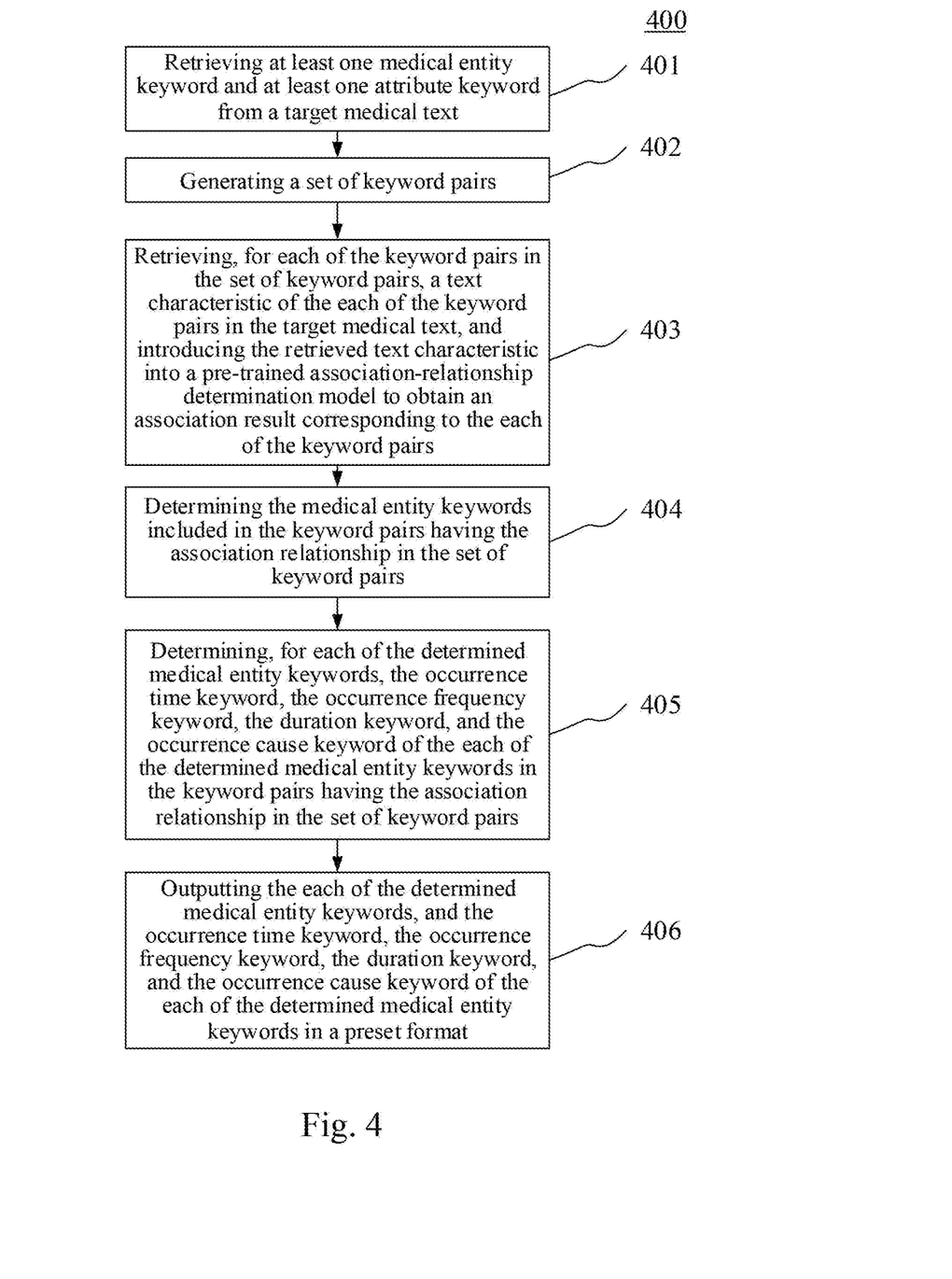
FIG. 4 is a process diagram of another embodiment of a method for outputting information according to the disclosure.

Further referring to FIG. 4, a process 400 of another embodiment of a method for outputting information is shown. The process 400 of the method for outputting information includes:

Step 401: retrieving at least one medical entity keyword and at least one attribute keyword from a target medical text.

In the embodiment, an electronic device (e.g., the server shown in FIG. 1) on which the method for outputting information runs may retrieve at least one medical entity keyword and at least one attribute keyword from a target medical text.

In the embodiment, relevant descriptions in the step 201 of the embodiment shown in FIG. 2 may be referred to for specific descriptions on the target medical text, the medical entity, and the medical entity keyword, which are not repeated any more here.

In the embodiment, the attribute keyword may include at least one of following items: an occurrence time keyword, an occurrence frequency keyword, a duration keyword, or an occurrence cause keyword. The occurrence time keyword, the occurrence frequency keyword, the duration keyword, and the occurrence cause keyword are a keyword describing an occurrence time attribute of a medical entity, a keyword describing an occurrence frequency attribute of the medical entity, a keyword describing a duration attribute of the medical entity, and a keyword describing an occurrence cause attribute of the medical entity respectively.

In the embodiment, the electronic device may first retrieve at least one medical entity keyword from a target medical text, and then retrieve at least one attribute keyword from the target medical text; or the electronic device may first retrieve at least one attribute keyword from the target medical text, and then retrieve at least one medical entity keyword from the target medical text.

In the embodiment, relevant descriptions in the step 201 of the embodiment shown in FIG. 2 may be referred to for specific descriptions on how to retrieve the medical entity keyword from the target medical text, which are not repeated any more here.

In some optional implementations of the embodiment, the retrieving at least one attribute keyword from a target medical text may include: retrieving the at least one attribute keyword from the target medical text based on a preset regular expression. In practice, in order to retrieve the occurrence time keyword, the occurrence frequency keyword, the duration keyword, and the occurrence cause keyword from the target medical text, the occurrence time keyword, the occurrence frequency keyword, the duration keyword, and the occurrence cause keyword may be retrieved from the target medical text respectively based on a preset regular expression of occurrence time, a regular expression of occurrence frequency, a regular expression of duration, and a regular expression of occurrence cause.

In some optional implementations of the embodiment, the retrieving at least one attribute keyword from a target medical text may be introducing the target medical text into a pre-trained occurrence time keyword retrieval model, a pre-trained occurrence frequency keyword retrieval model, a pre-trained duration keyword retrieval model, and a pre-trained occurrence cause keyword retrieval model respectively, to obtain the occurrence time keyword, the occurrence frequency keyword, the duration keyword, and the occurrence cause keyword of the target medical text, where the occurrence time keyword retrieval model, the occurrence frequency keyword retrieval model, the duration keyword retrieval model, and the occurrence cause keyword retrieval model are used for characterizing the corresponding relationship between the medical text and the occurrence time keyword, the corresponding relationship between the medical text and the occurrence frequency keyword, the corresponding relationship between the medical text and the duration keyword, and the corresponding relationship between the medical text and the occurrence cause keyword respectively. Relevant descriptions on the training the medical entity keyword retrieval model in the embodiment shown in FIG. 2 may be referred to for the methods for training the occurrence time keyword retrieval model, the occurrence frequency keyword retrieval model, the duration keyword retrieval model, and the occurrence cause keyword retrieval model, which are not repeated any more here.

Step 402: generating a set of keyword pairs.

Step 403: retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs.

Specific operations in the steps 402, and 403 in the embodiment are basically identical to those in the steps 202, and 203 in the embodiment shown in FIG. 2, and are not repeated any more here.

Step 404: determining the medical entity keywords included in the keyword pairs having the association relationship in the set of keyword pairs.

In the embodiment, the electronic device may determine the medical entity keywords included in the keyword pairs having the association relationship in the set of keyword pairs.

Here, the keyword pairs having the association relationship in the set of keyword pairs refer to the each of the keyword pairs in the set of keyword pairs in the step 403. A text characteristic of the each of the keyword pairs is retrieved from the target medical text and introduced into a pre-trained association-relationship determination model to obtain the association result corresponding to the each of the keyword pairs. If the association result corresponding to the each of the keyword pairs is that the keyword pair has the association relationship, then the keyword pair is a keyword pair having the association relationship; and if the association result corresponding to the each of the keyword pairs is that the keyword pair does not have the association relationship, then the keyword pair is a keyword pair not having the association relationship.

Step 405: determining, for each of the determined medical entity keywords, the occurrence time keyword, the occurrence frequency keyword, the duration keyword, and the occurrence cause keyword of the each of the determined medical entity keywords in the keyword pairs having the association relationship in the set of keyword pairs.

The attribute keyword is retrieved in the step 401 by retrieving the occurrence time keyword, the occurrence frequency keyword, the duration keyword, and the occurrence cause keyword based on different retrieval methods (e.g., different regular expressions or different attribute keyword retrieval models). Therefore, each attribute keyword retrieved in the step 401 may be determined as the occurrence time keyword, the occurrence frequency keyword, the duration keyword, or the occurrence cause keyword. Thus, for each of the determined medical entity keywords, the keyword pairs including a medical entity keyword identical to the keyword may be found in the keyword pairs having the association relationship in the set of keyword pairs, and an occurrence time keyword, an occurrence frequency keyword, a duration keyword, and an occurrence cause keyword in the attribute keywords included in the found keyword pairs may be determined as the occurrence time keyword, the occurrence frequency keyword, the duration keyword, and the occurrence cause keyword of the each of the determined medical entity keywords. As will be appreciated, if the attribute keywords included in the found keyword pairs do not include an occurrence time keyword, an occurrence frequency keyword, a duration keyword, or an occurrence cause keyword, then the absent occurrence time keyword, occurrence frequency keyword, duration keyword or occurrence cause keyword may be set as a preset character string, for example, set as "N.A."

Step 406: outputting the each of the determined medical entity keywords, and the occurrence time keyword, the occurrence frequency keyword, the duration keyword, and the occurrence cause keyword of the each of the determined medical entity keywords in a preset format.

In the embodiment, the electronic device may output the each of the determined medical entity keywords, and the occurrence time keyword, the occurrence frequency keyword, the duration keyword, and the occurrence cause keyword of the each of the determined medical entity keywords in a preset format. For example, the each of the determined medical entity keywords, and the occurrence time keyword, the occurrence frequency keyword, the duration keyword, and the occurrence cause keyword of the each of the determined medical entity keywords may be outputted as a set of information.

As an example, for a target medical text "recently chest pain frequently occurs, and lasts for about a few minutes each time. Nausea often occurs in the last month," following contents may be outputted:

Medical entity keyword: chest pain
Occurrence time keyword: recently
Occurrence frequency keyword: frequently occur
Duration keyword: about a few minutes
Occurrence cause keyword: N.A.
Medical entity keyword: nausea
Occurrence time keyword: last month
Occurrence frequency keyword: often
Duration keyword: N.A.
Occurrence cause keyword: N.A.

As can be seen from FIG. 4, compared with the embodiment corresponding to FIG. 2, the process 400 of the method for outputting information in the embodiment highlights that the attribute keyword includes at least one of an occurrence time keyword, an occurrence frequency keyword, a duration keyword, or an occurrence cause keyword, and highlights outputting each of the medical entity keywords included in the keyword pairs having the association relationship in a set of keyword pairs, and the occurrence time keyword, the occurrence frequency keyword, the duration keyword, and the occurrence cause keyword of the each medical entity keyword in a preset format. Thus, the solution described in the embodiment can improve the abundance of outputted information contents to a greater extent.

Figure 5:
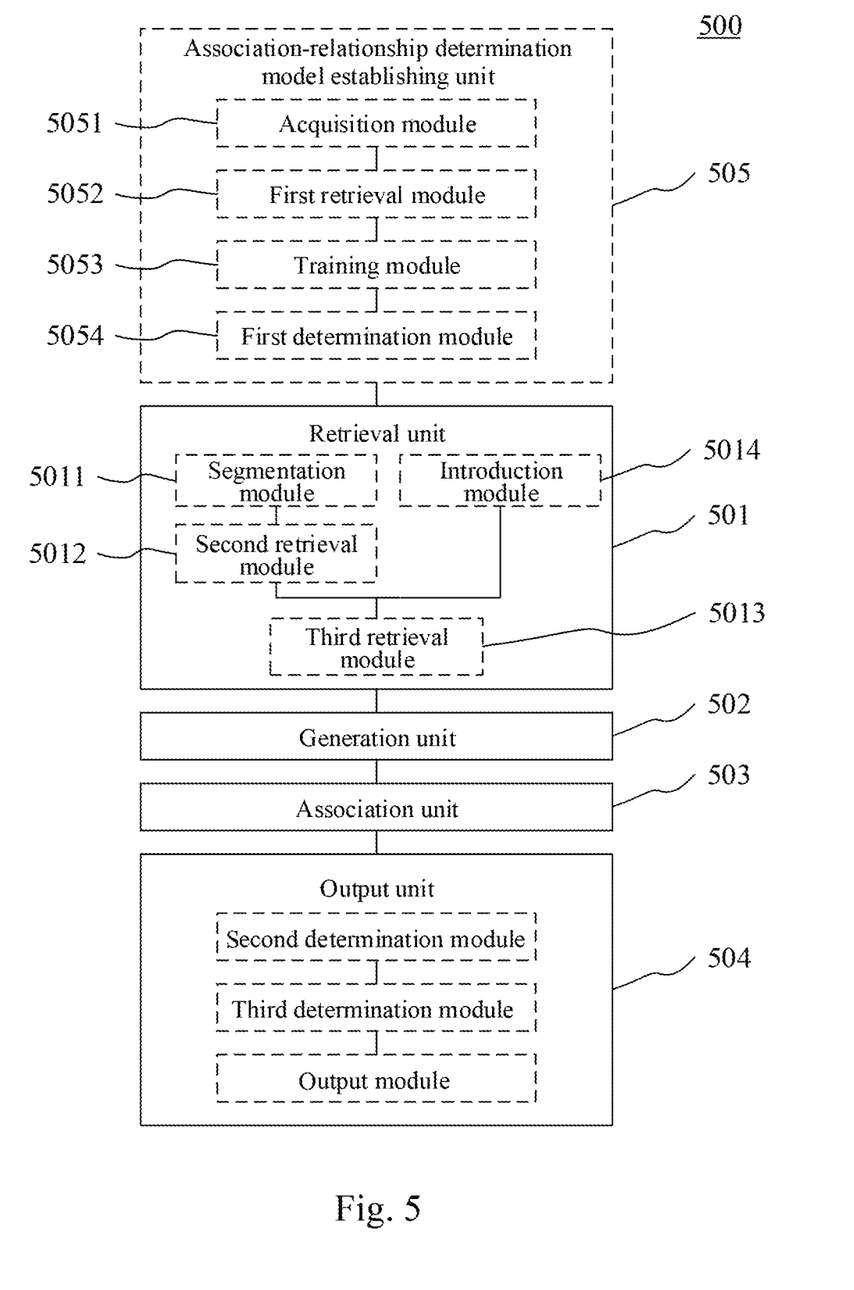
FIG. 5 is a structural schematic diagram of an embodiment of an apparatus for outputting information according to the disclosure.

Further referring to FIG. 5, as an implementation of the method shown in the above figures, the disclosure provides an embodiment of an apparatus for outputting information. The embodiment of the apparatus corresponds to the embodiment of the method shown in FIG. 2. The apparatus may be specifically applied to a variety of electronic devices.

As shown in FIG. 5, an apparatus 500 for outputting information according to the embodiment includes: a retrieval unit 501, a generation unit 502, an association unit 503, and an output unit 504. The retrieval unit 501 is configured for retrieving at least one medical entity keyword and at least one attribute keyword from a target medical text; the generation unit 502 is configured for generating a set of keyword pairs, where a keyword pair includes the retrieved medical entity keyword and the retrieved attribute keyword; the association unit 503 is configured for retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, where the association result is used for indicating whether an association relationship exists between two words in a word pair, and the association-relationship determination model is used for characterizing a corresponding relationship between the text characteristic and the association result; and the output unit 504 is configured for outputting the keyword pairs having the association relationship in the set of keyword pairs.

Relevant descriptions on the steps 201, 202, 203 and 204 in the embodiment corresponding to FIG. 2 may be referred to respectively for specific processing of the retrieval unit 501, the generation unit 502, the association unit 503, and the output unit 504 of the apparatus 500 for outputting information according to the embodiment and technical effects brought thereby, which are not repeated any more here.

In some optional implementations of the embodiment, the apparatus 500 may further include an association-relationship determination model establishing unit 505. The association-relationship determination model establishing unit 505 includes: an acquisition module 5051, configured for acquiring an initial association-relationship determination model and a predetermined set of sample data, where each of the sample data in the set of sample data includes a medical text, at least one sample word pair corresponding to the medical text and a word-pair annotation result corresponding to the sample word pair, the sample word pair includes the medical entity keyword and the attribute keyword in the medical text, and the word-pair annotation result is used for indicating whether the association relationship exists between the medical entity keyword and the attribute keyword in the sample word pair; a first retrieval module 5052, configured for retrieving, for the each of the sample data in the set of sample data, and for each of the at least one sample word pair in the each of the sample data, the text characteristic of the each of the at least one sample word pair in the medical text of the each of the sample data; a training module 5053, configured for training the initial association-relationship determination model using a machine learning method with the text characteristic of the each of the at least one sample word pair in the each of the sample data in the set of sample data in the medical text of the each of the sample data as input data, and the word-pair annotation result corresponding to the each of the at least one sample word pair as corresponding output data; and a first determination module 5054, configured for determining the trained initial association-relationship determination model as the pre-trained association-relationship determination model.

In some optional implementations of the embodiment, the association-relationship determination model may include at least one of following items: a gradient boosting decision tree, a support vector machine, or a neural network.

In some optional implementations of the embodiment, the retrieval unit 501 may include: a tokenizer module 5011, configured for tokenizing the target medical text to obtain a token sequence; and a second retrieval module 5012, configured for retrieving the at least one medical entity keyword from the token sequence based on a preset medical entity keyword dictionary.

In some optional implementations of the embodiment, the retrieval unit 501 may further include: a third retrieval module 5013, configured for retrieving the at least one attribute keyword in the target medical text based on a preset regular expression.

In some optional implementations of the embodiment, the retrieval unit 501 may further include: an introduction module 5014, configured for introducing the target medical text into a pre-trained medical entity keyword retrieval model to obtain the at least one medical entity keyword, where the medical entity keyword retrieval model is used for characterizing a corresponding relationship between the medical text and the medical entity keyword.

In some optional implementations of the embodiment, the medical entity keyword retrieval model may include a long short-term memory network model, or a conditional random field model.

In some optional implementations of the embodiment, the attribute keyword may include at least one of following items: an occurrence time keyword, an occurrence frequency keyword, a duration keyword, or an occurrence cause keyword.

In some optional implementations of the embodiment, the output unit 504 may include: a second determination module 5041, configured for determining the medical entity keywords included in the keyword pairs having the association relationship in the set of keyword pairs; a third determination module 5042, configured for determining, for each of the determined medical entity keywords, the occurrence time keyword, the occurrence frequency keyword, the duration keyword, and the occurrence cause keyword of the each of the determined medical entity keywords in the keyword pairs having the association relationship in the set of keyword pairs; and an output module 5043, configured for outputting the each of the determined medical entity keywords, and the occurrence time keyword, the occurrence frequency keyword, the duration keyword, and the occurrence cause keyword of the each of the determined medical entity keywords in a preset format.

It should be noted that the descriptions on other embodiments in the disclosure may be referred to for implementation details and technical effects of the units in the apparatus for outputting information according to the embodiment of the disclosure, which are not repeated anymore here.

Figure 6:
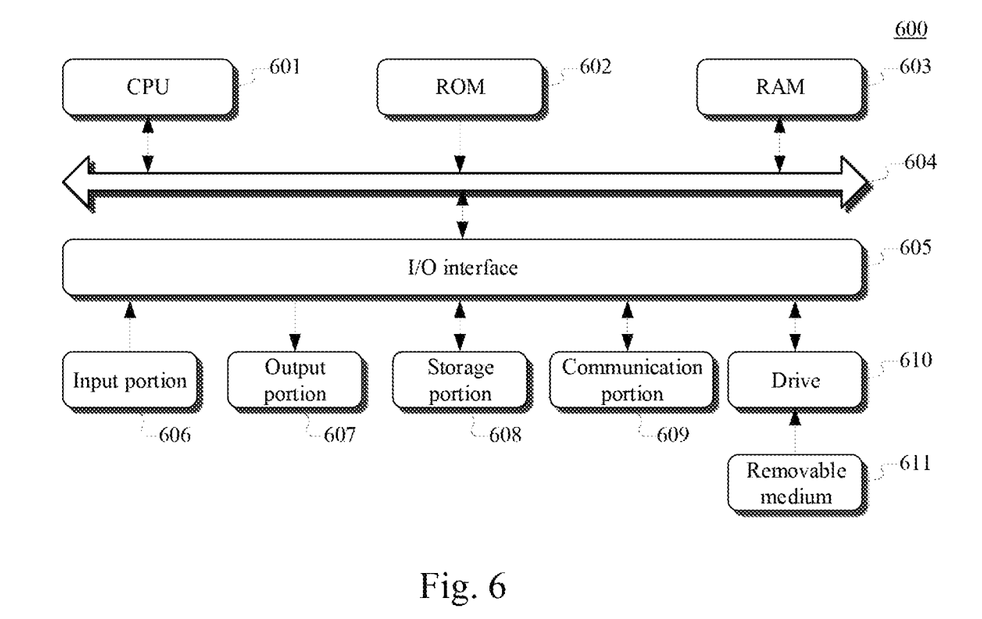
FIG. 6 is a structural schematic diagram of a computer system suitable for implementing an electronic device according to an embodiment of the disclosure.

Further referring to FIG. 6, a structural schematic diagram of a computer system 600 suitable for implementing an electronic device according to an embodiment of the disclosure is shown. The electronic device shown in FIG. 6 is only an example, and should not limit the functions and scope of application of the embodiment of the disclosure in any way.

As shown in FIG. 6, the computer system 600 includes a central processing unit (CPU) 601, which may execute various appropriate actions and processes in accordance with a program stored in a read-only memory (ROM) 602 or a program loaded into a random access memory (RAM) 603 from a storage portion 608. The RAM 603 also stores various programs and data required by operations of the system 600. The CPU 601, the ROM 602 and the RAM 603 are connected to each other through a bus 604. An input/output (I/O) interface 605 is also connected to the bus 604.

The following components are connected to the I/O interface 605: an input portion 606 including a keyboard, a mouse etc.; an output portion 607 comprising a cathode ray tube (CRT), a liquid crystal display device (LCD), a speaker etc.; a storage portion 608 including a hard disk and the like; and a communication portion 609 comprising a network interface card, such as a LAN card and a modem. The communication portion 609 performs communication processes via a network, such as the Internet. A drive 610 is also connected to the I/O interface 605 as required. A removable medium 611, such as a magnetic disk, an optical disk, a magneto-optical disk, and a semiconductor memory, may be installed on the drive 610, to facilitate the retrieval of a computer program from the removable medium 611, and the installation thereof on the storage portion 608 as needed.

In particular, according to embodiments of the present disclosure, the process described above with reference to the flow chart may be implemented in a computer software program. For example, an embodiment of the present disclosure includes a computer program product, which comprises a computer program that is tangibly embedded in a machine-readable medium. The computer program comprises program codes for executing the method as illustrated in the flow chart. In such an embodiment, the computer program may be downloaded and installed from a network via the communication portion 609, and/or may be installed from the removable media 611. The computer program, when executed by the central processing unit (CPU) 601, implements the above mentioned functionalities as defined by the methods of the present disclosure. It should be noted that the computer readable medium in the present disclosure may be computer readable storage medium. An example of the computer readable storage medium may include, but not limited to: semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fibre, a portable compact disk read only memory (CD-ROM), an optical memory, a magnet memory or any suitable combination of the above. In the present disclosure, the computer readable storage medium may be any physical medium containing or storing programs which can be used by a command execution system, apparatus or element or incorporated thereto. The computer readable medium may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the above.

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion comprising one or more executable instructions for implementing specified logic functions. It should also be noted that, in some alternative implementations, the functions denoted by the blocks may occur in a sequence different from the sequences shown in the figures. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system executing specified functions or operations, or by a combination of a dedicated hardware and computer instructions.

The units or modules involved in some embodiments of the present application may be implemented by means of software or hardware. The described units or modules may also be provided in a processor, for example, described as: a processor, comprising a retrieval unit, a generation unit, an association unit, and an output unit, where the names of these units or modules do not in some cases constitute a limitation to such units or modules themselves. For example, the generation unit may also be described as "a unit for generating a set of keyword pairs."

In another aspect, the present application further provides a non-transitory computer-readable storage medium. The non-transitory computer-readable storage medium may be the non-transitory computer-readable storage medium included in the apparatus in the above described embodiments, or a stand-alone non-transitory computer-readable storage medium not assembled into the apparatus. The non-transitory computer-readable storage medium stores one or more programs. The one or more programs, when executed by a device, cause the device to: retrieve at least one medical entity keyword and at least one attribute keyword from a target medical text; generate a set of keyword pairs, each of the keyword pairs including the retrieved medical entity keyword and the retrieved attribute keyword; retrieve, for each of the keyword pairs in the set of keyword pairs, a text characteristic of the each of the keyword pairs in the target medical text, and introduce the retrieved text characteristic into a pre-trained association-relationship determination model to obtain an association result corresponding to the each of the keyword pairs, the association result used for indicating whether an association relationship exists between two words in a word pair, and the association-relationship determination model used for characterizing a corresponding relationship between the text characteristic and the association result; and output the keyword pairs having the association relationship in the set of keyword pairs.

The above description only provides an explanation of the preferred embodiments of the present application and the technical principles used. It should be appreciated by those skilled in the art that the inventive scope of the present application is not limited to the technical solutions formed by the particular combinations of the above-described technical features. The inventive scope should also cover other technical solutions formed by any combinations of the above-described technical features or equivalent features thereof without departing from the concept of the disclosure. Technical schemes formed by the above-described features being interchanged with, but not limited to, technical features with similar functions disclosed in the present application are examples.

What is claimed is:

1. A method for outputting information, the method comprising:
    retrieving at least one medical entity keyword and at least one attribute keyword from a target medical text;
    generating a set of keyword pairs, each of the keyword pairs including the retrieved medical entity keyword and the retrieved attribute keyword;
    retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, the association result used for indicating whether an association relationship exists between two words in a word pair, and the association-relationship determination model used for characterizing a corresponding relationship between the text characteristic and the association result; and
    outputting the keyword pairs having the association relationship in the set of keyword pairs.

2. The method according to claim 1, wherein the method further comprises establishing the association-relationship determination model, the establishing the association-relationship determination model comprising:
    acquiring an initial association-relationship determination model and a predetermined set of sample data, wherein each of the sample data in the set of sample data comprises a medical text, at least one sample word pair corresponding to the medical text, and a word-pair annotation result corresponding to the sample word pair, the sample word pair includes the medical entity keyword and the attribute keyword in the medical text, and the word-pair annotation result is used for indicating whether the association relationship exists between the medical entity keyword and the attribute keyword in the sample word pair;
    retrieving, for the each of the sample data in the set of sample data, and for each of the at least one sample word pair in the each of the sample data, the text characteristic of the each of the at least one sample word pair in the medical text of the each of the sample data;
    training the initial association-relationship determination model using a machine learning method with the text characteristic of the each of the at least one sample word pair in the each of the sample data in the set of sample data in the medical text of the each of the sample data as input data, and the word-pair annotation result corresponding to the each of the at least one sample word pair as corresponding output data; and
    determining the trained initial association-relationship determination model as the pre-trained association-relationship determination model.

3. The method according to claim 2, wherein the association-relationship determination model comprises at least one of following items: a gradient boosting decision tree, a support vector machine, or a neural network.

4. The method according to claim 3, wherein the retrieving at least one medical entity keyword and at least one attribute keyword from a target medical text comprises:
    tokenizing the target medical text to obtain a token sequence; and
    retrieving the at least one medical entity keyword from the token sequence based on a preset medical entity keyword dictionary.

5. The method according to claim 4, wherein the retrieving at least one medical entity keyword and at least one attribute keyword from a target medical text comprises:
    retrieving the at least one attribute keyword from the target medical text based on a preset regular expression.

6. The method according to claim 3, wherein the retrieving at least one medical entity keyword and at least one attribute keyword from a target medical text comprises:
    introducing the target medical text into a pre-trained medical entity keyword retrieval model to obtain the at least one medical entity keyword, wherein the medical entity keyword retrieval model is used for characterizing a corresponding relationship between the medical text and the medical entity keyword.

7. The method according to claim 6, wherein the medical entity keyword retrieval model comprises a long short-term memory network model, or a conditional random field model.

8. The method according to claim 5, wherein the attribute keyword comprises at least one of following items: an occurrence time keyword, an occurrence frequency keyword, a duration keyword, or an occurrence cause keyword.

9. The method according to claim 8, wherein the outputting the keyword pairs having the association relationship in the set of keyword pairs comprises:
    determining the medical entity keywords included in the keyword pairs having the association relationship in the set of keyword pairs;
    determining, for each of the determined medical entity keywords, the occurrence time keyword, the occurrence frequency keyword, the duration keyword, and the occurrence cause keyword of the each of the determined medical entity keywords in the keyword pairs having the association relationship in the set of keyword pairs; and
    outputting the each of the determined medical entity keywords, and the occurrence time keyword, the occurrence frequency keyword, the duration keyword, and the occurrence cause keyword of the each of the determined medical entity keywords in a preset format.

10. An apparatus for outputting information, comprising:
at least one processor; and
a memory storing instructions, the instructions when executed by the at least one processor, cause the at least one processor to perform operations, the operations comprising:
retrieving at least one medical entity keyword and at least one attribute keyword from a target medical text;
generating a set of keyword pairs, each of the keyword pairs including the retrieved medical entity keyword and the retrieved attribute keyword;
retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, the association result used for indicating whether an association relationship exists between two words in a word pair, and the association-relationship determination model used for characterizing a corresponding relationship between the text characteristic and the association result; and
outputting the keyword pairs having the association relationship in the set of keyword pairs.

11. The apparatus according to claim 10, wherein the operations further comprise establishing the association-relationship determination model, the establishing the association-relationship determination model comprising:
acquiring an initial association-relationship determination model and a predetermined set of sample data, wherein each of the sample data in the set of sample data comprises a medical text, at least one sample word pair corresponding to the medical text, and a word-pair annotation result corresponding to the sample word pair, the sample word pair includes the medical entity keyword and the attribute keyword in the medical text, and the word-pair annotation result is used for indicating whether the association relationship exists between the medical entity keyword and the attribute keyword in the sample word pair;
retrieving, for the each of the sample data in the set of sample data, and for each of the at least one sample word pair in the each of the sample data, the text characteristic of the each of the at least one sample word pair in the medical text of the each of the sample data;
training the initial association-relationship determination model using a machine learning method with the text characteristic of the each of the at least one sample word pair in the each of the sample data in the set of sample data in the medical text of the each of the sample data as input data, and the word-pair annotation result corresponding to the each of the at least one sample word pair as corresponding output data; and
determining the trained initial association-relationship determination model as the pre-trained association-relationship determination model.

12. The apparatus according to claim 11, wherein the association-relationship determination model comprises at least one of following items: a gradient boosting decision tree, a support vector machine, or a neural network.

13. The apparatus according to claim 12, wherein the retrieving at least one medical entity keyword and at least one attribute keyword from a target medical text comprises:
tokenizing the target medical text to obtain a token sequence; and
retrieving the at least one medical entity keyword from the token sequence based on a preset medical entity keyword dictionary.

14. The apparatus according to claim 13, wherein the retrieving at least one medical entity keyword and at least one attribute keyword from a target medical text comprises:
retrieving the at least one attribute keyword from the target medical text based on a preset regular expression.

15. The apparatus according to claim 12, wherein the retrieving at least one medical entity keyword and at least one attribute keyword from a target medical text comprises:
introducing the target medical text into a pre-trained medical entity keyword retrieval model to obtain the at least one medical entity keyword, wherein the medical entity keyword retrieval model is used for characterizing a corresponding relationship between the medical text and the medical entity keyword.

16. The apparatus according to claim 15, wherein the medical entity keyword retrieval model comprises a long short-term memory network model, or a conditional random field model.

17. The apparatus according to claim 14, wherein the attribute keyword comprises at least one of following items: an occurrence time keyword, an occurrence frequency keyword, a duration keyword, or an occurrence cause keyword.

18. The apparatus according to claim 17, wherein the outputting the keyword pairs having the association relationship in the set of keyword pairs comprises:
determining the medical entity keywords included in the keyword pairs having the association relationship in the set of keyword pairs;
determining, for each of the determined medical entity keywords, the occurrence time keyword, the occurrence frequency keyword, the duration keyword, and the occurrence cause keyword of the each of the determined medical entity keywords in the keyword pairs having the association relationship in the set of keyword pairs; and
outputting the each of the determined medical entity keywords, and the occurrence time keyword, the occurrence frequency keyword, the duration keyword, and the occurrence cause keyword of the each of the determined medical entity keywords in a preset format.

19. A non-transitory computer-readable storage medium storing a computer program, the computer program when executed by one or more processors, causes the one or more processors to perform operations, the operations comprising:
retrieving at least one medical entity keyword and at least one attribute keyword from a target medical text;
generating a set of keyword pairs, each of the keyword pairs including the retrieved medical entity keyword and the retrieved attribute keyword;
retrieving, for each of the keyword pairs in the set of keyword pairs, a text characteristic of the each of the keyword pairs in the target medical text, and introducing the retrieved text characteristic into a pre-trained association-relationship determination model to obtain an association result corresponding to the each of the keyword pairs, the association result used for indicating whether an association relationship exists between two words in a word pair, and the association-relationship determination model used for characterizing a corresponding relationship between the text characteristic and the association result; and outputting the keyword pairs having the association relationship in the set of keyword pairs.

\* \* \* \* \*

UNITED STATES PATENT AND TRADEMARK OFFICE
CERTIFICATE OF CORRECTION

| | |
|---|---|
| PATENT NO. | : 10,496,748 B2 |
| APPLICATION NO. | : 16/134641 |
| DATED | : December 3, 2019 |
| INVENTOR(S) | : Jingbo Zhou et al. |

Page 1 of 1

It is certified that error appears in the above-identified patent and that said Letters Patent is hereby corrected as shown below:

On the Title Page

Add item (30):
--Foreign Application Priority Date: October 18, 2017 CN 201710972236.5--

Signed and Sealed this
Twenty-fourth Day of March, 2020

Andrei Iancu
*Director of the United States Patent and Trademark Office*